United States Patent [19]
Bingham et al.

[11] 4,160,092
[45] Jul. 3, 1979

[54] QUINAZOLINONE OXIDES AND THEIR USE AS INTERMEDIATES FOR PHARMACEUTICAL AGENTS

[75] Inventors: Elena M. Bingham, Wilmington, Del.; Arthur J. Elliott, Cedar Grove, N.J.

[73] Assignee: E. I. Du Pont de Nemours and Company, Wilmington, Del.

[21] Appl. No.: 807,074

[22] Filed: Jun. 16, 1977

[51] Int. Cl.$^2$ .......................................... C07D 239/82
[52] U.S. Cl. .............................. 544/286; 260/239.3 B; 260/308 A; 260/562 B; 260/566 A; 424/244; 424/269
[58] Field of Search .................. 260/251 QB; 544/286

[56] References Cited
U.S. PATENT DOCUMENTS

3,723,432   3/1973   Ott ................................. 260/251 QB

OTHER PUBLICATIONS

Culvenor–"Reviews of Pure & Applied Chemistry," vol. 3, 1953 (p. 86).
Sulkowski et al. - J. Org. Chem. 27, 4424–4425 (1962).

*Primary Examiner*—Raymond V. Rush

[57] ABSTRACT

1-Methyl-6-substituted-4-phenyl-quinazolin-2-one-3-oxides and their use as intermediates in the preparation of 3-fluorobenzodiazepines which are useful as tranquilizers, muscle relaxants and sedatives.

6 Claims, No Drawings

QUINAZOLINONE OXIDES AND THEIR USE AS INTERMEDIATES FOR PHARMACEUTICAL AGENTS

BACKGROUND OF THE INVENTION

Copending U.S. Pat. application Ser. No. 687,318, filed May 26, 1976 by Elena M. Bingham and William Joseph Middleton, which is a continuation-in-part of U.S. Pat. application Ser. No. 597,502, now abandoned, discloses certain novel 3-fluorobenzodiazepines of the formula:

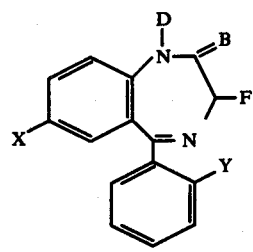
IV where
X is Cl, Br, NO$_2$, or CF$_3$;
Y is H, Cl, Br or F;
D is H, hydrocarbyl of 1–4 carbons, —CH$_2$CF$_3$, —CONHR, —CH$_2$CH$_2$NR$_2$, or —CH$_2$CH$_2$NR$_2$.A, where R is alkyl of 1–4 carbons and A is a pharmaceutically suitable acid;
B is O; or
B and D together is =N—N=C(R')—
where R' is H or C$_1$–C$_4$ alkyl, and the use of such compounds as tranquilizers, muscle relaxants and sedatives in mammals. In addition, Bingham and Middleton disclose a process for making such compounds by reaction of the corresponding 3-hydroxybenzodiazepine with a dialkylaminosulfur trifluoride as follows:

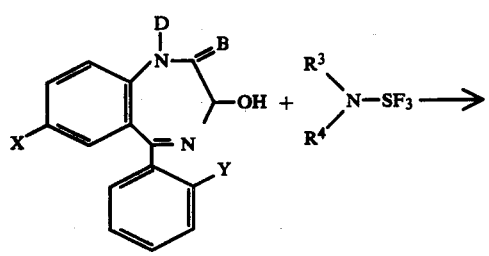

where R$^3$ and R$^4$ are a primary alkyl group of 1–4 carbons or taken together are —(CH$_2$)$_4$— or —(CH$_2$)$_5$.

In addition, copending U.S. Pat. application Ser. No. 807,075, filed simultaneously with the present application by William Joseph Middleton discloses an improved process for preparing such 3-fluorobenzodiazepines, which improved process can be summarized schematically by the following equations:

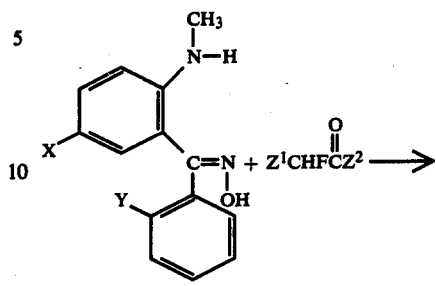

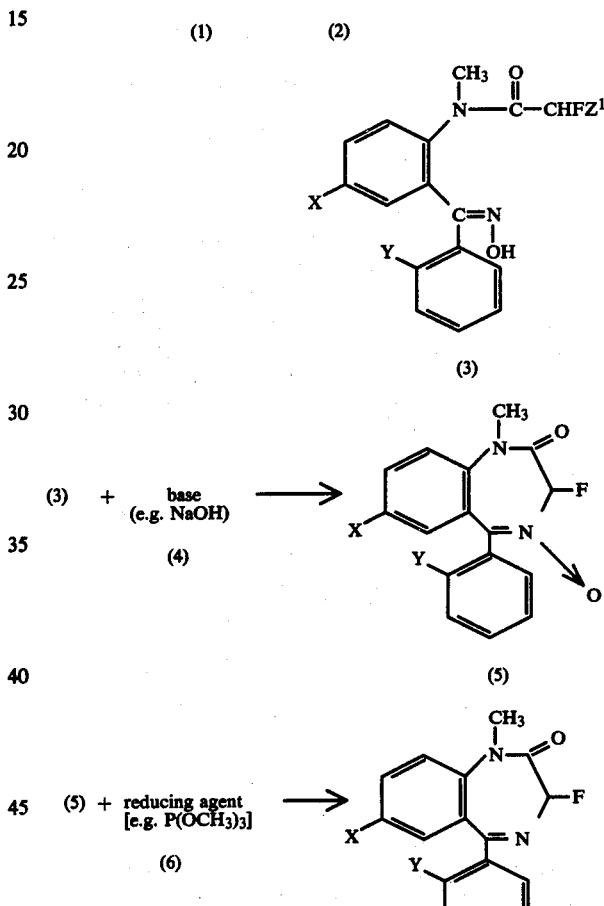

where
X is Cl, Br, NO$_2$ or CF$_3$;
Y is H, Cl, Br or F; and
Z$^1$ and Z$^2$ are Cl or Br.
Middleton also discloses that starting material (1) can be prepared by the process disclosed in U.S. Pat. No. 3,398,139.

SUMMARY OF THE INVENTION

The present invention relates to an improved process for making such N-methylaminobenzophenone antioximes, and novel intermediates used in the improved process.

More specifically, the present invention relates to a new process for the preparation of N-methylaminobenzophenone anti-oximes by alkylation, and subsequent hydrolysis, of the corresponding quinazoline oxides.

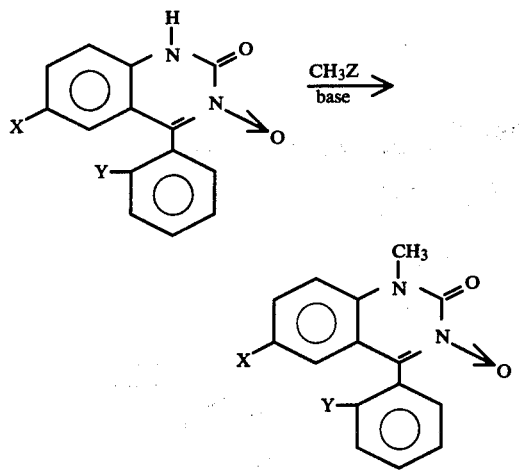

The preparation of compounds of formula III is accomplished in two interrelated stages. The first stage involves treating the alkali metal salt of quinazolinone 3-oxides of Formula I (X = Cl, Br, $CF_3$ or $NO_2$; Y = H, Br, Cl or F) with alkylating agents of formula $CH_3Z$; (Z = I, Cl, Br, $CF_3SO_2O—$, $FSO_2O—$, $CCl_3SO_2O—$ or $CH_3OSO_2O—$) to give 1-methylquinazoline 3-oxides of Formula II (X and Y as defined).

The reaction products of Formula II (X, Y as defined) are then hydrolytically converted in the presence of base to the methylaminobenzophenone anti-oximes of Formula III (X, Y as defined).

DETAILED DESCRIPTION OF THE INVENTION

Preferred compounds

Compounds from within the scope of U.S. Patent Application Serial Number 687,318 which are preferred for their activity are those shown in formula IV where, independently:
B = O.
X = Cl;
D = H;
D = $C_1$–$C_3$ alkyl;
X = Cl and D = H;
X = Cl and D = $C_1$–$C_3$ alkyl.
More preferred are those compounds where:
X = Cl or Br;
Y = H, Cl, or F;
D = H, —$CH_3$, or —$C_2H_5$; and
B = O.

Most preferred are those compounds where:
X = Cl or Br;
Y = H or F;
D = $CH_3$; and
B = O.

Necessarily, then, compounds of formula II which are preferred as intermediates are those where X is chlorine or bromine. More preferred compounds of formula II are those where X is chlorine or bromine and Y is hydrogen, chlorine or fluorine.

Most preferred compounds are those where X is chlorine or bromine and Y is hydrogen or fluorine.

Specifically preferred are the following compounds: 6-chloro-1-methyl-4-phenyl-2(1H)quinazolinone 3-oxide; 6-bromo-1-methyl-4-phenyl-2(1H)quinazolinone 3-oxide.

1-Methylquinazolinone oxides of Formula II can be prepared by treating a solution or mixture of a compound of Formula I, prepared as taught by Sulkowski and Childress, J. Org. Chem, 27, 4424 (1962) or by the improved process disclosed by Middleton in copending U.S. Pat. application Ser. No. 807,076, filed simultaneously herewith and a suitable base with an alkylating agent in an inert organic solvent medium. The reaction is preferentially carried out at moderate temperatures of 50°–75°, but this step can be effected at room temperature or above. Suitable solvents include, but are not limited to, ethers such as tetrahydrofuran, diethyl ether and glyme; amides of secondary amines such as N,N-dimethylformamide and N,N-dimethylacetamide. Representative bases useful in the generation of the alkali metal salt of a compound of Formula I include, but are not limited to, potassium carbonate, sodium hydride, sodium carbonate and sodium or potassium alkoxides such as sodium ethoxide or methoxide.

The alkylated quinazolinone oxides can be isolated from the reaction mixture by conventional means, such as filtration of the insoluble product.

The compounds of Formula II can then be converted to the anti-oxime by heating with a base in an aqueous-alcoholic solvent. The reaction is conveniently carried out at the reflux temperature of the solvent. Useful alcoholic solvents include, but are not limited to, ethanol, methanol, propanol, isopropanol, butanol, 2-methoxyethanol, ethylene glycol and propylene glycol. Examples of suitable bases are alkali metal (such as sodium and potassium) hydroxides, carbonates and bicarbonates.

The alkylaminobenzophenone anti-oximes obtained can be purified by evaporation of the reaction solvent and recrystallization of the solid residue.

The following examples further illustrate the improved process of the present invention and the synthesis of the novel compounds of formula II. Parts are by weight and temperatures are in degrees Centigrade unless otherwise stated.

EXAMPLE 1

6-Chloro-1-methyl-4-phenyl-2(1H)quinazolinone 3-Oxide

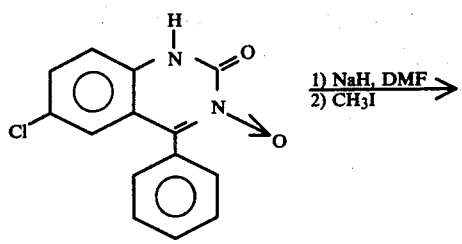

A mixture of 40 g (0.146 mole) of 6-chloro-4-phenyl-2(1H)quinazolinone 3-oxide in 1000 ml of N,N-dimethylformamide was treated with sodium hydride (7.7 g 50% in oil, 0.16 mole) and heated to 60°. The mixture was cooled to 10° and 30 g (0.211 mole) of methyl iodide was added during 5 min. The reaction mixture was stirred at room temperature for two hours and the solid collected by filtration, washed and dried. The crude solid (30.2 g) was recrystallized from N,N-dimethylformamide to give, in two crops, 24.3 g (58%) of yellow plates identified as 6-chloro-1-methyl-4-phenyl-2(1H)-quinazolinone 3-oxide: mp 289°–291°, Anal. Calcd for $C_{15}H_{11}ClN_2O_2$: C, 62.84; H, 3.87; N, 9.77; Found: C, 63.01; H, 3.84; N, 9.97.

EXAMPLE 2

5-Chloro-2-methylaminobenzophenone anti-Oxime

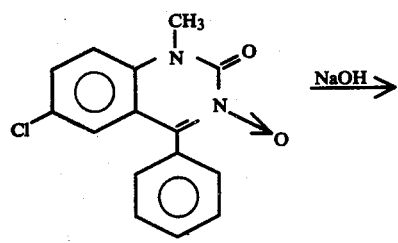

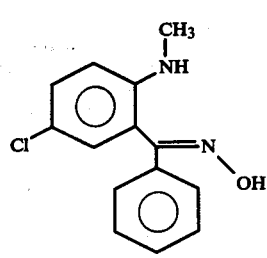

A mixture of 14.3 g (0.05 mole) of 6-chloro-4-phenyl-2(1H)quinazolinone 3-oxide, 200 ml of ethanol, 20 ml of water and 0.4 g (0.01 mole) of sodium hydroxide was refluxed for 2 hours, cooled and poured into ice water. The mixture was extracted twice with 250 ml of methylene chloride. The organic extracts were dried (MgSO$_4$) and evaporated to dryness. The residue was dissolved in 50 ml of 1-chlorobutane, filtered and diluted with hexane. A pale yellow solid precipitated and was collected by filtration to give 9.2 g (69%) of 5-chloro-2-methylaminobenzophenone anti-oxime: mp 90°–91°

Anal. Calcd for $C_{14}N_{13}N_2OCl$: C, 64.50; H, 5.03; N, 10.74; Found: C, 64.75; H, 4.92; N, 10.69.

EXAMPLE 3

6-Chloro-1-methyl-4-phenyl-2(1H)quinazolinone 3-Oxide

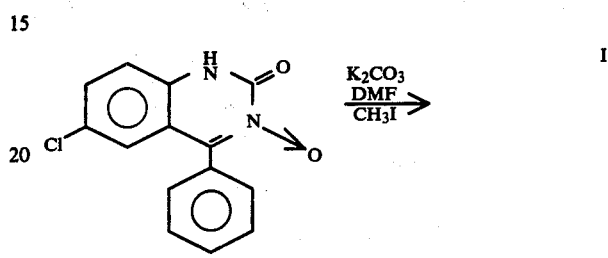

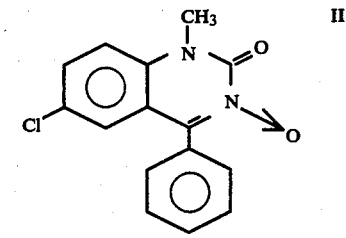

A mixture of 125 g (0.458 mole) of 6-chloro-4-phenyl-2(1H)quinazolinone 3-oxide, 3,250 ml of N,N-dimethylformamide and 75 g of powdered anhydrous potassium carbonate was heated to 50°. After heating for approximately 30 minutes at this temperature, an increased solubility of the suspended solid due to formation of the potassium salt of I was observed. At this point, 150 g (65.8 ml) of methyl iodide was added dropwise at a fast rate. The reaction with the methyl iodide was somewhat exothermic and caused the pot temperature to rise to 58°. Stirring at 50°–55° was continued for 1 hour. The contents of the flask were cooled and filtered and the solid obtained was thoroughly washed with water. The product, 6-chloro-1-methyl-4-phenyl-2(1H)quinazolinone 3-oxide was obtained in 80% yield (103.2 g), mp 253.5°–254°.

EXAMPLE 4

5-Chloro-2-methylaminobenzophenone anti-Oxime

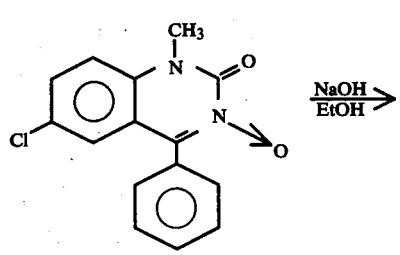

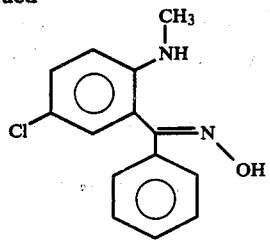

The 6-chloro-1-methyl-4-phenyl-2(1H)quinazolinone 3-oxide, 286.7 g (1 mole) was mixed with 2,000 ml of ethanol and 200 ml of a 1N NaOH solution was added. The mixture was refluxed for 2 hours, cooled and filtered to remove a small amount of sodium bicarbonate(~ 14 g). This ethanol solution was evaporated to dryness under reduced pressure (bath temp. not to exceed ~ 40°) to give a solid. Evacuation with a pump removed the last traces of ethanol.

The yellow solid was dissolved in 350 ml of hot 1-chlorobutane. This hot viscous solution was filtered through a coarse fritted glass funnel. The filter and empty flask were thoroughly rinsed with exactly 150 ml of 1-chlorobutane and added to the filtrate. A total of only 500 ml of 1-chlorobutane was used. On addition of 2,000 ml of hexane to the chlorobutane solution, the desired product precipitated out. The anti-5-chloro-2-(N-methylamino)benzophenone oxime was obtained either in 88% yield (crystalline form "a", mp 90°-91°) or 80% yield (crystalline form "b", mp 86°-88°) [200-230 g]. The anti-oxime obtained exists in two different crystalline modifications. Their solid infrared spectra differ, as do color and solubility. The least soluble crystalline form, "a" precipitates out immediately on addition of hexane to the 1-chlorobutane solution. It is quite yellow, fluffy and obtained in good yield. The crystalline form "b" is more soluble and is obtained when hexane addition does not cause rapid precipitation, but rather a slow crystallization which requires thorough cooling. The material is pale yellow and crystalline.

EXAMPLE 5

2-Chloro-5-methylaminobenzophenone anti-Oxime

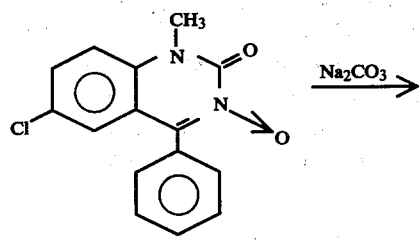

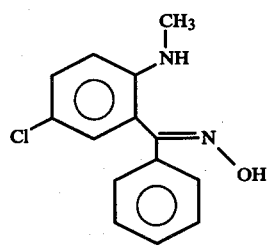

A mixture of 7.15 g (0.025 mole) of 6-chloro-1-methyl-4-phenyl-2(1H)quinazolinone 3-oxide, 100 ml of ethanol, 15 ml of water and 0.325 g (0.012 mole) of sodium carbonate was refluxed for 2 hours. The mixture was added to an equal volume of ice water and extracted with methylene chloride. The dried (MgSO4) organic extracts were evaporated to dryness and the residue dissolved in a minimum amount of 1-chlorobutane. Hexane was added, and the solution was cooled to give 3.44 g of 5-chloro-2-methylaminobenzophenone anti-oxime (mp 85°-86°).

EXAMPLE 6

6-Chloro-1-methyl-4-phenyl-2(1H)quinazolinone 3-Oxide

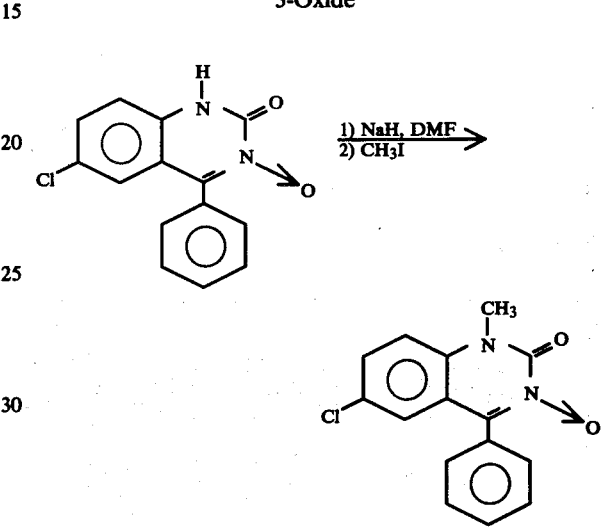

To a suspension of 5 g (0.018 mole) of 6-chloro-4-phenyl-2(1H)quinazolinone 3-oxide and 125 ml of N,N-dimethylformamide was added, at room temperature, 0.96 g of sodium hydride (50% in oil). The temperature rose to 30° and the stirring was continued for approximately 30 minutes to effect salt formation To this mixture was added, dropwise, 6 g (0.042 mole) of methyl iodide. Stirring was continued for approximately 2 hours and the solid was collected by filtration, washed with water and with 10 ml of 1N HCl to give 3.98 g (78%) of product identified as 6-chloro-1-methyl-4-phenyl-2(1H)-quinazoline 3-Oxide: mp 253°-254°. $^1$H nmr (CF$_3$CO$_2$H) δ 3.12 ppm (s, 3H); δ 6.5-7.3 (m, 8H, aromatic).

EXAMPLE 7

6-Bromo-1-methyl-4-phenyl-2(1H)quinazolinone 3-Oxide

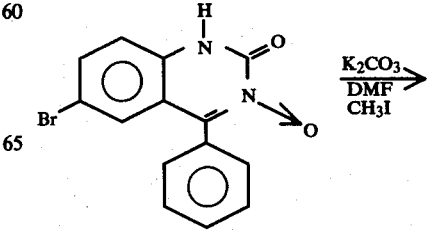

-continued

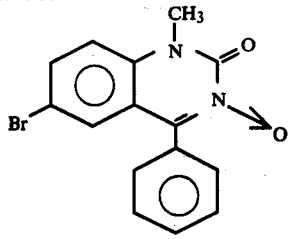

A mixture of 17 g (0.053 mole) of 6-bromo-4-phenyl-2(1H)quinazolinone 3-oxide, 400 ml of N,N-dimethylformamide and 9.1 g (0.065 mole) of powdered anhydrous potassium carbonate was heated to 50°. The contents of the flask were stirred at 50° for 30 minutes, at which time 8 ml (18 g) of methyl iodide was added dropwise at a fast rate. Stirring at 50°–55° was continued for one hour. The solid portion of the cooled mixture was collected by filtration and washed with water to give 13.07 g (74%) of yellow crystals identified as 6-bromo-1-methyl-4-phenyl-2(1H)quinazolinone 3-oxide: mp 279°–279.5°; $^1$H nmr (CF$_3$CO$_2$H) δ 3.05 (s, 3H), δ 6.5–7.5 ppm (m, 8H).

Anal. Calcd for C$_{15}$H$_{11}$BrN$_2$O$_2$: C, 54.40; H, 3.35; N, 8.46; Found: C, 54.24; H, 3.39; N, 8.79.

Table I shows additional 1-methylquinazolinone 3-oxides that can be prepared by the processes disclosed and illustrated above using the appropriate quinazolinone 3-oxide and a suitable methylating agent.

TABLE I

Preparation of Selected 1-Alkylquinazolinone 3-Oxides

| Quinazolinone 3-Oxide | Alkylating Agent | Product |
|---|---|---|
| (6-bromo, 2'-fluoro phenyl derivative, N-H) | + CH$_3$I → | (6-bromo, 2'-fluoro phenyl derivative, N-CH$_3$) |
| (6-chloro, 2'-chloro phenyl derivative, N-H) | + (CH$_3$)$_2$SO$_4$ → | (6-chloro, 2'-chloro phenyl derivative, N-CH$_3$) |
| (6-chloro, phenyl derivative, N-H) | + CH$_3$I → | (6-chloro, phenyl derivative, N-CH$_3$) |
| (6-chloro, 2'-bromo phenyl derivative, N-H) | + FSO$_2$OCH$_3$ → | (6-chloro, 2'-bromo phenyl derivative, N-CH$_3$) |

Table II shows additional methylaminobenzophenone anti-oximes that can be prepared by the processes disclosed and illustrated above using the appropriate 1-methylquinazolinone 3-oxide and a suitable base.

TABLE II
Preparation of Selected Alkylaminobenzophenone anti-Oximes
| 1-Alkylquinazolinone-3-oxide | Base | anti-Oxime |
|---|---|---|
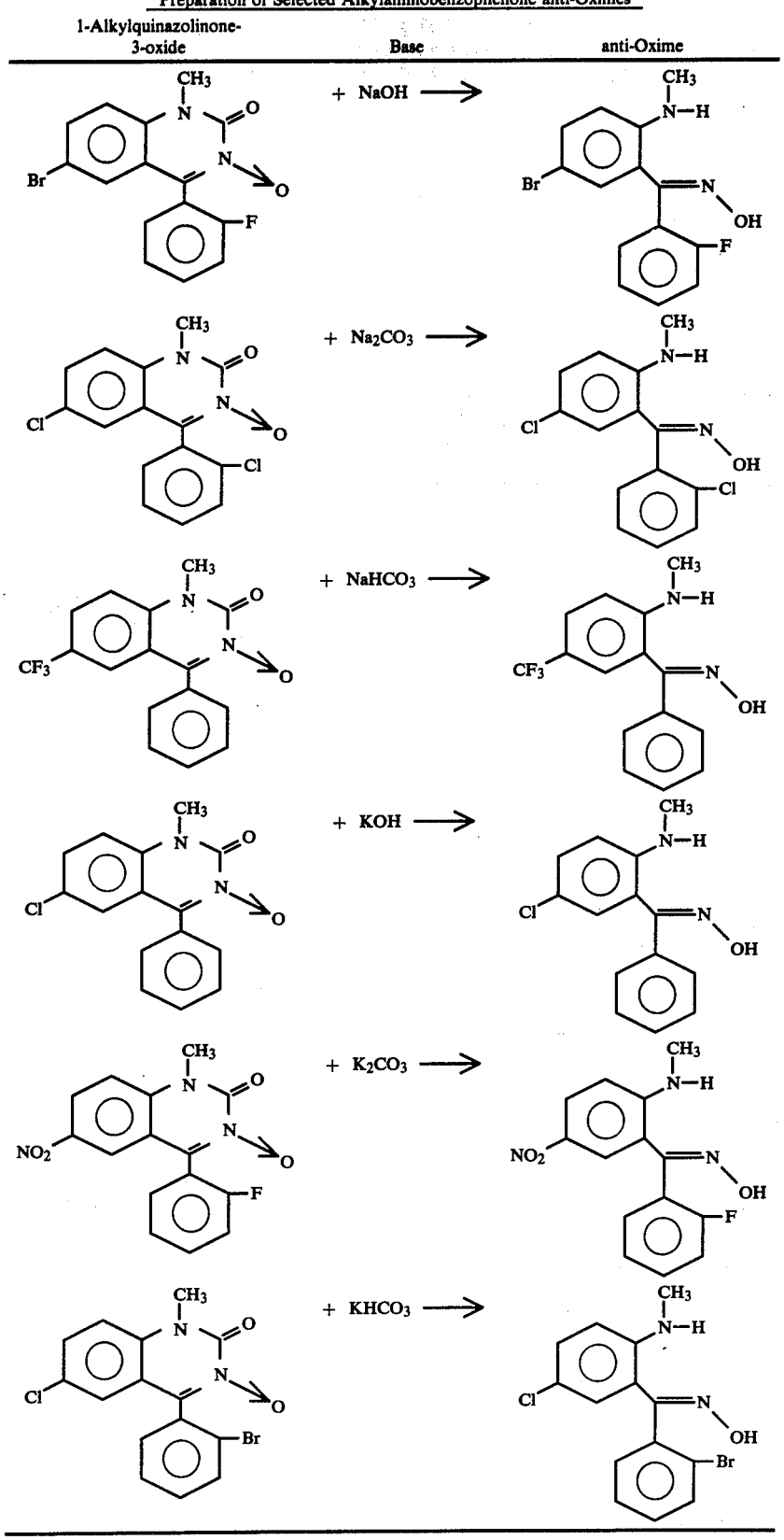
We claim:
1. A compound of the formula:

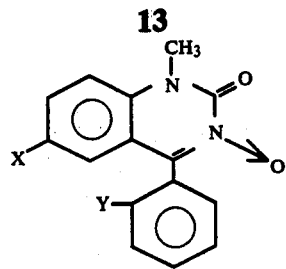
where
X is Cl, Br, NO₂ or CF₃; and
Y is H, Br, Cl, or F.
2. A compound of claim 1 where X is chlorine or bromine.
3. A compound of claim 1 where Y is hydrogen, chlorine or fluorine.
4. A compound of claim 2 where Y is hydrogen, chlorine or fluorine.
5. A compound of claim 2 where Y is hydrogen or fluorine.
6. The compound of claim 1 where X is chlorine and Y is hydrogen.
* * * * *